United States Patent [19]

Tracy et al.

[11] Patent Number: 5,922,671
[45] Date of Patent: Jul. 13, 1999

[54] ANIONIC SURFACTANTS HAVING MULTIPLE HYDROPHOBIC AND HYDROPHILIC GROUPS

[75] Inventors: David James Tracy; Ruoxin Li, both of Plainsboro, N.J.; Jean-Marc Ricca, Paris, France

[73] Assignee: Rhodia Inc., Cranbury, N.J.

[21] Appl. No.: 08/991,162

[22] Filed: Dec. 16, 1997

Related U.S. Application Data

[62] Division of application No. 08/777,706, Dec. 20, 1996, Pat. No. 5,710,121
[60] Provisional application No. 60/009,075, Dec. 21, 1995.

[51] Int. Cl.$^6$ ............... C11D 1/06; C11D 1/08; C11D 1/29; C11D 1/34
[52] U.S. Cl. .......... 510/467; 510/488; 510/495; 558/24; 558/156; 562/488
[58] Field of Search .................. 510/467, 488, 510/495; 558/24, 156; 562/488

[56] References Cited

U.S. PATENT DOCUMENTS

| | | | |
|---|---|---|---|
| 4,936,551 | 6/1990 | Behler et al. | 260/400 |
| 5,160,450 | 11/1992 | Okahara et al. | 252/174.21 |
| 5,487,778 | 1/1996 | Kaiser | 106/287.23 |
| 5,493,050 | 2/1996 | Varadaraj et al. | 562/41 |
| 5,507,863 | 4/1996 | Kaiser | 106/20 R |

FOREIGN PATENT DOCUMENTS

| | | |
|---|---|---|
| 42 32 414 | 3/1994 | Germany . |
| 4401 565 | 7/1994 | Germany . |
| 432 1022 | 1/1995 | Germany . |
| 44409328 | 5/1996 | Germany . |
| 60-203935 | 10/1985 | Japan . |
| PCT/93/25646 | 12/1993 | Japan . |
| 6-19038 | 1/1994 | Japan . |
| 1503280 | 3/1978 | United Kingdom . |
| PCT/JP93/00811 | 7/1993 | WIPO . |

OTHER PUBLICATIONS

Rosen, M. Geminis: A New Generation of Surfactants Chemtech 30–33 Mar. (1993).
Stapersma, et. al. Hydroxyalkane Sulfonate, a New Surfactant Based on Olefins JAOCS 69; No. 1, (1992) 39–43.
Herke, et. al. Addition of Bisulfite to α–Olefins: Synthesis of n–Alkane Sulfonates; JAOCS; 69, No. 1 (1992) 47–51.
Jiang, et. al. The Effect of Hydrophobic–Lipophilic Interactions on Chemical Reactivity Reactivity. J. Am. Chem. Soc. 106 (1984) 7202–7205.
Vold, M. Micellization, Some Properties of Dimers of Na–Octyl Sulfates; J. Colloid and Interface Sci; 135 No. 2 (1990) 520–530.
Menger, et. al. Binding Properties of 1–Pyrenesulfonic Acid in Water. J. Org. Chem.Soc. 52 No. 17 (1987) 3793–98.
Neumann, et. al. The Interaction of Cationic Dyes with Anionic Surfactants in the Premicellar Region. J. Colloid and Interface Sci. 135; No. 1 (1990) 209–217.

Cheng, et. al. Facial Amphiphiles. J. Am. Chem. Soc. 114 No. 18 (1992) 7319–20.
Jaeger, et. al. Double–chain Surfactants with Two Carboxylate Head Groups That Form Vesicles. Langmuir, 12 No. 8; (1996) 1976–80.
Okano, et. al. α–Sulfonated Fatty Acid Esters JAOCS 73 No. 1 (1996) 31–37.
Zhu, et. al. Preparation and Properties of Double Chain Surfactants Bearing Two Sulfonate Groups. Jpn. Oil Chem. Soc. 40 vol. 6 (1991) 473–477.
Zhu, et. al. Preparation and Surface Active Properties of New Amphipathic Compounds with Two Phosphate Groups and Two Long Chain Alkyl Groups. JAOCS; 68 No. 4, (1991) 268–71.
Paubert, et. al. Sulphonates Derived from Dimer Acids and Esters. Tenside Surf. Det. 32 No. 1 (1995) 36–44.
Furhop, et. al. Bolaamphiphiles and Monolayer Lipid Membranes; J. Am. Chem. Soc. 108 No. 8 (1986) 1785–91.
Ikeda, et al. Re–examination of Aggregation Behavior of Disodium 1,12–Dodecane Disulfate. J. Colloid and Interface Sci 130 No. 1 (1989) 290–91.
Rosen, et. al. Relationship of Structure to Properties of Surfactants: LDS JAOCS 69 N O.1 (1992) 30–33.
Zhu, et. al. Preparation and Surface Active Properties of Amphipathic Compounds with Two Sulfate Groups and Two Lipophile Alkyl Chains. JAOCS 67 No. 7 (1990) 459–463.

(List continued on next page.)

*Primary Examiner*—Margaret Einsmann
*Assistant Examiner*—John R. Hardee
*Attorney, Agent, or Firm*—Craig M. Bell; John Daniel Wood

[57] ABSTRACT

Mild and environmentally benign bis-alkylphenol alkoxylated gemini surfactants of the formula:

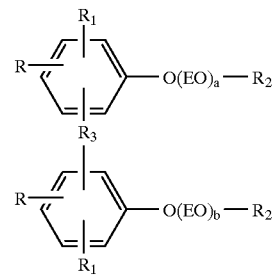

wherein R independently represents alkali, $R_1$ independently represents hydrogen EO represents ethyleneoxy radicals alkyl, $R_2$ independently represents hydrogen, $—SO_3M$, $—P(O)(OM)_2$, $—CH_2COOM$, $—CH_2CHOHCH_2—SO_3HM$, wherein M represents hydrogen, alkyl or alkaline earth metal, ammonium or an organic base salt; $R_3$ represents alkylene of from one to about 10 carbon atoms or $—C(O)—R_4—C(O)—$ wherein $R_4$ represents alkylene or aryl, and $—O—R_5—O—$ wherein $R_5$ represents aliphatic or aromatic moieties with the proviso that when $R_3$ is alkylene, then $R_2$ is not hydrogen, and a and b are numbers ranging from one to about 100, with the proviso that when $R_2$ is hydrogen, b is not zero.

26 Claims, No Drawings

OTHER PUBLICATIONS

Zhu, et. al. Synthesis and Properties of Bis (Sulfonate) Types of Double Chain Surfactants. J. Jpn. Oil Chem. Soc. 42 No. 2 (1993) 86–94.

Zhu, et. al. Preparation and Properties of Glycerol Based Double or Triple Chain Surfactants with Two Hydrophilic Groups. JAOCS 69; No. 7 1992) 626–632.

Zhu, et. al. Preparation and Surface Active Properties of New Amphipathic Compounds with Two Phosphate Groups and Two Long–Chain Alkyl Groups. JAOCS No. 4 (1991) 268–271.

Zhu, et. al. Preparation and Properties of Double or Triple Chain Surfactants with Two Sulonfate Groups. JAOCS; 68 No. 7 1991) 539–543.

Stein, et. al. Synthesis and Aggregation Properties of a New Family of Amphiphiles with Unusual Headgroups. J. Am. Chem. Soc. 114 No. 10; (1992) 3943–3950.

Zhu, et. al. Double–Chain Surfactants with Two Carboxylate Groups and Their Relation to Similar Double–Chain Compounds J. Colloid and Interface Sci. 158 (1993) 40–45.

Okahara, et. al. Surface Active Properties of New Types of Amphiphatic Compounds with Two Hydrophilic Ionic Groups and Two Lipophilic Alkyl Chains J. Jpn. Oil Chem. Soc. 37; No. 9 (1988) 746–747.

Ono, et. al. Preparation and Properties of Bis (Sodium Carboxylate) Types of Cleavable Surfactants Derived from Diethyl Tartrate and Fatty Carbonyl Compounds J. Jpn. Oil Chem. Soc. 42 No. 1 (1993) 10–16.

Gao, et. al. Dynamic Surface Tension of Aqueous Surfactant Solutions.6. JAOCS 71 No. 7 (1994) 771–776.

Masuyama, et. al. Synthesis and Properties of Bis (Taurine) Types of Double Chain Surfactants J. Jpn. Oil Chem. Soc. 41 No. 4 (1992) 13–17.

Kida, et. al. A Facile Synthesis of Polyglycidyl Ethers from Polyols and Epichlorohydrin. Synthesis (May 1993) 487–489.

Tanaka, et. al. Double Chain Surfactant as a New and Useful Micelle Reagent for Electrokinetic Chromatography J. Chromatogr. 648 (1993) 469–473.

English abstracts of JP references, Jan. 1994.

ANIONIC SURFACTANTS HAVING MULTIPLE HYDROPHOBIC AND HYDROPHILIC GROUPS

This application claims priority from U.S. provisional application serial No. 60/009,075, filed Dec. 21, 1995. This application is a divisional of application Ser. No. 08/777,706, filed Dec. 20, 1996, now U.S. Pat. No. 5,710,121.

This invention relates to a novel group of anionic surfactants having at least two hydrophobic moieties and at least two hydrophilic groups per molecule.

BACKGROUND OF THE INVENTION

Anionic surfactants carry a negative charge on the hydrophilic portion, usually in the form of a carboxylate, phosphate, sulfate or sulfonate. These surfactants find use in emulsion polymerization as well as in agricultural chemicals, personal care and household products, industrial and institutional cleaners. They function as emulsifiers, cleaners, wetting agents, foaming and frothing agents such as for shampoos, car washes, carpet shampoos, hand dishwashing, latex foaming, oil recovery and other industrial uses.

While surfactants generally have one hydrophilic group and one hydrophobic moiety, recently a group of compounds having two hydrophobic moieties and two hydrophilic groups have been introduced. These have become known as "Gemini surfactants" in the literature (*Chemtech*, March 1993, pp 30–33), and *J. American Chemical Soc.*, 115, 10083–10090, (1993) and the references cited therein. Other surfactant compounds having two hydrophilic groups and two hydrophobic moieties have been disclosed but not referred to as Gemini surfactants.

It is known to sulfate, phosphate and carboxylate surfactants through functionalization of the hydroxyls.

However, secondary hydroxyl's undergo sulfation, phosphation or carboxylation poorly, leading to undesired by-products and/or high levels of acid or low product yields. The compounds of the invention contain primary hydroxyl groups which can be more efficiently functionalized.

There is also a need for new and more effective and efficient surfactants, as well as the need for mild surfactants which are biologically compatible in an ecologically sensitive environment. A new class of compounds has been developed which demonstrates improved surface-active properties that are further characterized as mild, and environmentally benign.

SUMMARY OF THE INVENTION

According to the invention, an improved class of anionic surfactants have been provided comprising compounds of the formula:

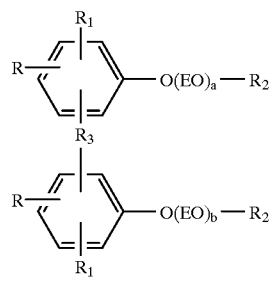

wherein R independently represents alkyl of from about 4 to about 20 carbon atoms, $R_1$ independently represents hydrogen and alkyl of from about 4 to 20 carbon atoms; $R_2$ independently represents —$SO_3M$, —$P(O)(OM)_2$, —$CH_2COOM$, —$CH_2CHOHCH_2SO_3M$, wherein M is hydrogen, alkali metal such as sodium, potassium, ammonium or organic base salt; and $R_3$ represents alkylene of from one to about 10 carbon preferably from about 1 to about 4 atoms or —C(O)—$R_4$—C(O)— wherein $R_4$ represents alkylene of from 1 to about 10 carbon atoms and aryl, e.g. phenylene. $R_3$ also represents —O—$R_5$—O— wherein $R_5$ represents aliphatic or aromatic moieties of from 1 to about 10 carbon atoms. EO represents ethyleneoxy radicals, a is a number of from 0 to about 100 preferably one from about 0 to about 30. Preferably, $R_3$ is alkylene and more preferably —$CH_2$. As used herein the terms "alkyl" or "alkylene" include straight as well as branched chains.

When compared to the corresponding conventional anionic surfactants, the novel compounds of the present invention show two unexpected surface active properties; unusually low critical micelle concentration (CMC) showing exceptional surfactant effectiveness and $pC_{20}$ values that exhibit exceptional surfactant efficiency in aqueous media. These properties are a measure of the tendency of the surfactant to form micelles and adsorb at the interface respectfully, and consequently, to reduce surface tension.

Preferably, R is alkyl of from about 6 to about 10 carbon atoms, and $R_1$ is preferably hydrogen. The organic base salts of the compounds of the invention can be illustrated by monoethanolamine, diethanolamine, triethanolamine, triethylamine, trimethylamine, N-hydroxyethyl morpholine and the like.

More specifically, the compounds of the present invention comprise:

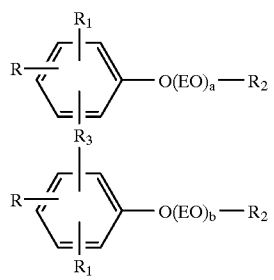

II

-continued

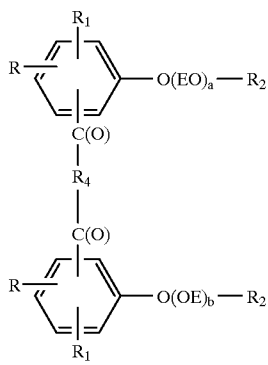

III

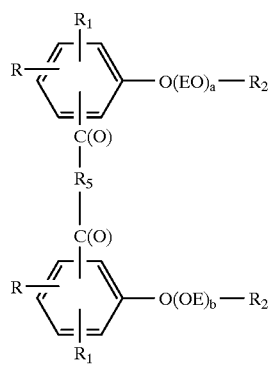

IV wherein R, $R_1$, $R_2$, $R_4$, a, and $R_5$ are as defined hereinbefore. $R_3$ represents alkylene, preferably methylene. It is noted that when $R_2$ is hydrogen or capped according to procedures well known in the art for preparing alkoxylated nonionic surfactants, the compounds are nonionic and are, although considered as included in the generic invention, they would be claimable as separate and distinct species. Compounds which are nonalkoxylated have been found to be particularly effective in blends such as with silicone compounds.

The primary hydroxyl group of the nonionic surfactants of this invention can be readily phosphated, sulfonated or carboxylated by standard techniques.

In addition to new compounds, the invention also discloses novel synergistic compositions when the compounds of the invention are blended with other surfactants.

DETAILED DESCRIPTION OF THE INVENTION

The compounds of the invention can be prepared by a variety of synthetic routes. The compounds of Formula II can be prepared by condensing a monoalkyl phenol with paraformaldehyde in the presence of an acid catalyst such as acetic acid. The compounds of Formula III can be synthesized by a Lewis acid catalyzed reaction of an alkylphenol with a dicarboxylic acid, e.g., terephthalic acid or succinic acid. The compounds of Formula IV can be synthesized by a base catalyzed reaction of an alkyldihydroxybenzene with a dibromide.

These products can be oxyalkylated by reacting the product with an alkylene oxide according to known methods, preferably in the presence of an alkaline catalyst. The free hydroxyl groups of the phenol or the alkoxylated derivative can then be sulfated, phosphated or carboxymethylated using normal methods such as sulfation with sulfamic acid or chlorosulfonic acid or sulfur trioxide, or carboxymethylated with an acylating agent such as a chloroacetic acid.

For alkylation conditions and commonly used alkylating agents, see Amphoteric Surfactants Vol. 12, Ed. B. R. Bluestein and C. L. Hilton, *Surfactant Science Series* 1982, pg. 17 and references cited therein, the disclosures of which are incorporated herein by reference.

For sulfation and phosphation, the reaction product of the paraformadehyde and the phenol can be reacted with a sulfating or phosphating agent such as sulfur trioxide, sulfamic acid, chlorosulfonic acid or phosphoric anhydride to form the compounds of the invention (Sulfation techniques are discussed in Surfactant Science Series, Vol 7, Part 1, S. Shore & D. Berger, page 135, the disclosure of which is incorporated herein by reference. For phosphating review see Surfactant Science Series, Vol 7, Part II, E. Jungermann & H. Silbrtman, page 495, the disclosure of which is incorporated herein by reference.)

Since the surfactants of the invention exhibit an extremely low critical micelle concentration (CMC) as compared with conventional surface-active agents because of the presence of two hydrophobic moieties and two hydrophilic groups in their molecule and since they are able to fully reduce surface tension and are highly soluble in water, the surfactants of the invention are extremely effective in aqueous solution at low concentrations. The surfactants of the invention can be used in any amount needed for a particular application which can be easily determined by a skilled artisan without undue experimentation.

The surfactants of the invention can be used alone as the essential hydrotrope component.

It has been unexpectedly found that blends of the compounds of the invention with certain conventional well known anionic, nonionic, cationic and amphoteric surfactants provide synergistic effects in relation to critical micelle concentration and surface tension reducing ability.

Examples of the nonionic surfactants usable herein include fatty acid glycerine and polygycerine esters, sorbitan sucrose fatty acid esters, higher alcohol ethylene oxide adducts, polyoxyethylene alkyl and alkyl allyl ethers, polyoxyethylene lanolin alcohol, glycerine and polyoxyethylene glycerine fatty acid esters, polyoxyethylene propylene glycol and sorbitol fatty acid esters, polyoxyethylene lanolin, castor oil or hardened castor oil derivatives, polyoxyethylene fatty acid amides, polyoxyethylene alkyl amines, an alkylpyrrolidone, glucamides, alkylpolyglucosides, mono- and dialkanol amides. Examples of the anionic surfactants used herein include fatty acid soaps, ether carboxylic acids and salts thereof, alkane sulfonate salts, α-olefin sulfonate salts, sulfonate salts of higher fatty acid esters, higher alcohol sulfate ester or ether ester salts, higher alcohol phosphate ester and ether ester salts, condensates of higher fatty acids and amino acids, and collagen hydrolysate derivatives.

Examples of the cationic surfactants used herein include alkyltrimethylammonium salts, dialkyldimethylammonium salts, alkyldimethylbenzylammonium salts, alkylpyridinium salts, alkylisoquinolinium salts, benzethonium chloride, and acylamino acid type cationic surfactants.

Examples of the amphoteric surfactants used herein include amino acid, betaine, sultaine, phosphobetaines, imidazoline type amphoteric surfactants, soybean phospholipid, and yolk lecithin.

Any of commonly used auxiliary additives such as inorganic salts such as Glauber salt and common salt, builders, humectants, solubilizing agents, UV absorbers, softeners, chelating agents, and viscosity modifiers may be added to the surfactants of the invention or blends thereof with other surfactants as disclosed herein.

The anionic surfactants of the invention are extremely mild and non-irritating to both eyes and skin and exhibit low toxicity; exhibit enhanced wetting speed, greater surface tension reduction, high foaming and foam stabilization properties, and excellent compatibility with other surfactants. The products of the invention are stable over a wide pH range and are biodegradable. These properties make these surfactants adaptable for use in products ranging from cosmetics to industrial applications, such as for non-irritating shampoos, e.g., baby shampoos, body shampoos, bubble baths, bar soaps, bath gels, hair conditioning gels, lotions, skin creams, make up removal creams, liquid detergents, and other washing and cosmetic products that contact the skin. The surfactants of the invention can also find use as hard surface cleaners including cars, dishes, toilets, floors, and the like; laundry detergents and soaps, metal working aids and the like.

It has also been unexpectedly found that the compounds of the invention particularly nonalkoxylated compounds are particularly useful in novel superwetting compositions containing an organosilicone compound(s) which can be represented by the general formula:

MDyD'xM            Formula V wherein M represents $Me_3SiO_{1/2}$ (represents $Me_3SiO$ or $Me_3Si$ as necessary to form a chemically complete structure); D represents $Me_2SiO$; D' represents MeRSiO; Me equals $CH_3$; R equals $C_nH_{2n}O(C_2H_4O)_a(C_3H_6O)_bR'$; y ranges from about 0 to 5, preferably zero; x ranges from about 1 to 5, preferably 1; n ranges from about 2 to 4, preferably 3; a ranges from about 3 to 25, preferably 3 to 15; and b ranges from about 0 to 25, preferably 0 to 15; it being understood that the oxyalkylene groups may be random and/or block mixtures; and R' can be hydrogen, an alkyl group having 1 to 4 carbon atoms, or an alkyl ester group wherein the alkyl group of the ester has 1 to 4 carbon atoms. Each R' can be same or different on any given molecule. Preferably, R' is hydrogen or a methyl group.

These organosilicone compounds can be represented by the following examples:

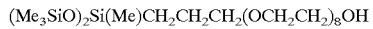

(Me₃SiO)₂Si(Me)CH₂CH₂CH₂(OCH₂CH₂)₈OH

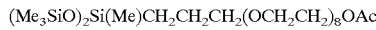

(Me₃SiO)₂Si(Me)CH₂CH₂CH₂(OCH₂CH₂)₈OAc

Me₃SiOSi(Me)₂OSi(Me)₂OSi(Me)₂CH₂CH₂CH₂(OCH₂CH₂)₈OH

(Me₃SiO)₂Si(Me)CH₂CH₂CH₂(OCH₂CH₂)₇.₅OMe

The most preferred organosilicone compound is represented by the following formula:

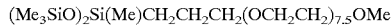

(Me₃SiO)₂Si(Me)CH₂CH₂CH₂(OCH₂CH₂)₇.₅OMe also known as SILWET L-77.

This is more fully disclosed in copending U.S. patent application Ser. No. 08/576,749, of Gao, et al., filed on even date herewith the present application, the entire disclosure of which is incorporated herein by reference.

Examples of the present invention are given below by way of illustration and not by way of limitation. All parts and percents are by weight unless otherwise stated.

EXAMPLE I

Preparation of 2,2'methylenebis[4(1,1,3,3-tetramethylbutyl)phenol].

Dissolve 4-(1,1,3,3-tetramethylbutyl phenol [724 g. 3.51 mole] in a minimum amount of xylene at room temperature in a three necked round bottom flask. Paraformaldehyde (15 g. 0.5 mol) and glacial acetic acid (100 mL.) were added slowly to the solution under argon. Reaction temperature was slowly raised to 135° C. (about 150° C. external temperature) as the solution was stirred vigorously. Water generated during the reaction was collected by Dean-Stark apparatus. After stirring 5 hours at 135° C., GC analysis indicated complete reaction. The reaction was stopped by distilling out all starting materials under reduced pressure at 150° C. The final pure product was obtained by washing the crude product twice with hexane in the flask. The white solid product was collected by filtration. Melting point of the final compound is 153° C. The NMR agreed with the structure. Lit. M.P. 152–153° C. (Brit J. Pharmacol, 10, 73–86 (1955)).

Also prepared according to the method of example I were:

a) 2,2'methylenebis(4-nonylphenol) was prepared in a similar manner by replacement of the 1,1,3,3,-Tetramethylbutylphenol by 4-nonylphenol in the same mole ratio to formaldehyde.

b) 2,2'methylenebis(4-dodecylphenol) was prepared by replacing 1,1,3,3-Tetramethylbutylphenol with 4-dodecylphenol at the same mole ratio.

c) 2,2'methylenebis[4,6-di(1,1-dimethylpropyl) phenol] was prepared by replacing 1,1,3,3-Tetramethylbutylphenol with 2,4-di(1,1-dimethylpropyl)phenol at the same mole ratio. (see U.S. Pat. No. 2,675,366).

EXAMPLE II

Preparation of 2,2'methylenebis[4-(1,1,3,3-tetramethylbutyl)phenol]ethoxylate:

Potassium hydroxide flakes (0.545 g) were added to a melted methylene bisoctylphenol (436 g) in a tarred beaker under nitrogen. Once the KOH was dissolved in it the solution was carefully poured into a preheated 7.57 (2 gallon) reactor. The reactor was degassed by pulling vacuum releasing with Nitrogen. Ethylene oxide (2–3 moles) was quickly added allowing for reaction kick. The remaining ethylene oxide (a total of 880 g) was added at 150–160° C. and 90 psig max. After 30 minutes the pressure remained constant, the reaction was cooled to 120° C. and vacuum stripped with slight nitrogen sparge for 20 minutes. Finally acetic acid was added to a pH of 7 to neutralize KOH. Analysis by NMR indicated 20 moles ethylene oxide had reacted. Cloud point (1% aqueous) was 68° C.

The following ethoxylates were prepared according to the method of Example II.

a) 2,2'methylenebis[4-(1,1,3,3-Tetramethylbutyl)phenol] 2EO was prepared in a similar manner except that 2 moles of ethylene oxide was used per mole of 2,2'methylenebis(1,1,3,3-Tetramethylbutylphenol). Cloud point 1% aqueous <0° C.

b) 2,2'methylenebis[4-(1,1,3,3-Tetramethylbutyl)phenol] 18 EO was prepared in a similar manner except that 18 moles of ethylene oxide was used per mole methylenebis(octylphenol) in Example II. Cloud point 1% aqueous 64° C.

c) 2,2'methylenebis[4-(1,1,3,3-Tetramethylbutyl)phenol] 10 EO was prepared in a similar manner except that 10 moles of ethylene oxide was used per mole of methylenebis(octylphenol). Cloud point 1% aqueous 6° C.

d) 2,2'methylenebis[4,6-di(1,1-dimethylpropyl)phenol] 16 EO was prepared in a similar manner except that 16 moles of ethylene oxide and 2,2'methylenebis[4,6-di(1,1-dimethylpropyl)phenol] was used instead of 2,2'methylenebis[4-(1,1,3,3-Tetramethylbutyl)phenol].

e) 2,2'methylenebis(4-nonylphenol) 20 EO was prepared in a similar manner except that methylenebis (nonylphenol) was used instead of methylenebis (octylphenol) and 20 moles of ethylene oxide was added per mole methylenebis(nonylphenol). Cloud point 1% aqueous 53° C.

EXAMPLE III
PREPARATION OF SULFATE SODIUM SALTS

Gemini sulfate sodium salts were prepared by the following process:

Ethoxylated methylene bis(octylphenol) (10 g. 8.9 mmol) was flushed with argon at 110° C. for 20 minutes. Sulfur trioxide pyridine complex dissolved in Dimethylformamide was added to the solution at 40° C. After temperature was brought up to 70° C., the reaction mixture was stirred for 8 hours at this temperature. Once TLC indicated that all starting material disappeared, the reaction was slowly poured into ice/$Na_2CO_3$ water solution. The pH of solution was maintained around 10 during the process. The reaction product was extracted twice with n-butanol. After evaporation of solvent, ethanol was added to the residue to remove inorganic salts by filtration. After evaporation of alcohol in the filtrate, the leftover solid was washed with ether twice again. The final pure product was collected by filtration.

The NMR agreed with the structure.

EXAMPLE IV
PREPARATION OF SULFATE AMMONIUM SALTS

Gemini sulfate ammonium salts were prepared by the following process:

Ethoxylated (20EO) methylenebis(octylphenol) (24.85 g.) was bubbled with argon at 120° C. for 30 minutes. After temperature was cooled to 60° C., dicyandiamide (0.08 g.) was added. Stirring of the mixture was continued for another 20 minutes. Sulfamic acid (4.24 g) was added to the mixture. The reaction was stirred at 140° C. for 7 hours. By that time, TLC (chloroform:methanol:water=4:2:trace) showed that the starting material disappeared. The reaction was cooled to 70° C. and pH adjusted to 9 by adding a small amount of monoethanolamine. The NMR agreed with the structure.

EXAMPLE V
PREPARATION OF PHOSPHATE ESTERS

Phosphate Esters salts were prepared by the following procedure:

Methylenebis(octylphenol)sodium phosphate: A solution of Triethylamine (1.43 g, 14.15 mmol), methylene bis (octylphenol) (3.0 g, 7.0 mmol) in dry hexane/THF was added dropwise to a solution of phosphorous oxychloride (1.30 mL, 14.15 mmol) in small amount of hexane under argon at –5° C. A white precipitate appeared. After stirring 2.5 hours at 0° C., TLC ($CHCl_3$:$CH_3OH$=5:1) showed that all starting material disappeared, the reaction was stopped by filtered off triethylammonium chloride salt. The solvent in filtrate was evaporated under reduced pressure.

A solution of NaOH in ice water was added to the filtrate at 0° C. Final pH of the solution was about 13. The solution was stirred for two hours before it was extracted with n-butanol three times. After evaporating solvent, the solid product was washed with hot ethanol to remove inorganic salt. Ethanol was evaporated under reduced pressure, and the solid was washed with cold acetone again. The final white pure product was collected by filtration. This material was confirmed by $^1$H-NMR, $^{13}$C-NMR and P-NMR. The yield of reaction was 90%.

EXAMPLE VI

SURFACE ACTIVITIES

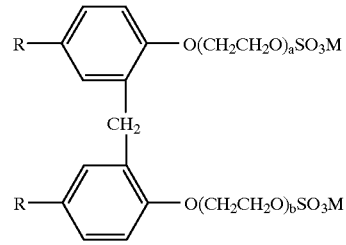

| a + b | R | M | Prepared by Method of Example | γcmc dyne/cm | CMC (M) | $pC_{20}$ | Draves wetting 0.1% (sec) |
|---|---|---|---|---|---|---|---|
| 0 | $C_8H_{17}$ | Na | III | 27.8 | $7.9 \times 10^{-5}$ | 5.8 | 5.7 |
| 2 | $C_8H_{17}$ | Na | III | 30.0 | $1.6 \times 10^{-5}$ | 6.1 | 20.6 |
| 2 | $C_8H_{17}$ | $NH_4$ | IV | 29.8 | $6.9 \times 10^{-6}$ | 6.2 | 30.0 |
| 18 | $C_8H_{17}$ | Na | III | 38.2 | $5.6 \times 10^{-6}$ | 6.3 | |
| 18 | $C_8H_{17}$ | $NH_4$ | IV | 36.0 | $3.4 \times 10^{-6}$ | 6.7 | |
| 22 | $C_8H_{17}$ | $NH_4$ | IV | 39.6 | $3.2 \times 10^{-6}$ | 6.3 | |

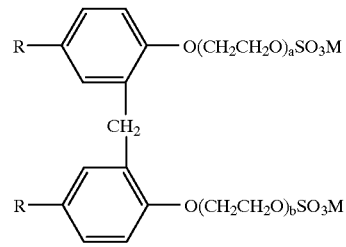

| a + b | R | M | Method | δdyne/cm |
|---|---|---|---|---|
| 0 | $C_8H_{17}$ | Na | V | 27.6 |
| 18 | $C_8H_{17}$ | Na | V | 29.1 |

The above data indicates that increased effectiveness (much lower CMC) and increased efficiency (higher $pC_{20}$ values) can be obtained by using the compounds of the invention.

EXAMPLE VII
IRRITATION

The products of this invention were evaluated for mildness by an In-Vitro Ocular Irritation (Eytex) study.

Alcohol sulfates and alcohol ether sulfates have eye irritancy properties which limit their use in personal care applications. Usually irritation ameliorating agents are used in combination with sulfates to minimize irritation. Compounds of this invention at 1% level have been shown to be minimal/mild when tested by the Eytex method.

Eytex Draize Equivalent (EDE)

0–15 Minimal

15–19 Minimal/Mild

19–22 Mild
22–25 Mild/Moderate
25–33 Moderate $$C_8H_{17}\text{—}\bigcirc\text{—}O(CH_2CH_2O)_aSO_3M$$
$$|$$
$$CH_2$$
$$|$$
$$C_8H_{17}\text{—}\bigcirc\text{—}O(CH_2CH_2O)_bSO_3M$$

| a + b | M | EDE |
|---|---|---|
| 2 | $NH_4$ | 15.8 |
| 13 | $NH_4$ | 16.0 |
| 0 | Na | 16.2 |

A standard laurylether (IEO) sulfate has a score of 27.1 under the same conditions.

By virtue of this property the surfactants of the invention can be used in personal care applications without the need for additional additives.

The above data indicates that increased effectiveness (much lower CMC) and increased efficiency (higher $pC_{20}$ values) can be obtained by using the compounds of the invention.

Thus when the surface properties for the compounds of the invention are compared to the corresponding conventional surfactants [$C_{12}H_{25}OCH_2CH_2OSO_3N_a$ has a cmc= $4.8 \times 10^{-3}$. See E. Gotte, 3rd Int. Congr. Surface Activity, Cologne, 1, 45 (1960)] such as shown in the Table, the novel compounds of the invention show two unexpected surface active properties; unusually low critical micelle concentration (CMC) and $pC_{20}$ values in aqueous media. These properties are a measure of the tendency of the surfactant to form micelles and adsorb at the interface, and consequently, to reduce surface tension respectively. The values shown in the Table demonstrate that the compounds of Example III, IV and V are one to two orders of magnitude (10–100 times) more efficient at reducing surface tension. For example, the $pC_{20}$ value for sodium lauryl ether (1EO) sulfate is 3.8. See J. A. Caskey; J. Colloid Interface Sci. 35, 46 (1971) and more than one order of magnitude (or >10 times) more efficient at forming micelles. This unusually high surface activity for these molecules is a result of their unique structure; the presence of two optimally spaced hydrophobic chains and hydrophilic groups. This molecular structure provides energetically favorable decreases in the free energy of adsorption and micellization through favorable distortion of water structure, and, at the same time, providing a "close packed" arrangement at the interface. The ability of the compounds of the invention to distort the water structure through inhibition of crystalline or liquid crystalline phase formation in bulk phase and at the same time to pack closely on adsorption at the interface is contrary to conventional wisdom. This again demonstrates the uniqueness of the molecular design for these compounds which is very critical to providing unexpected exceptional surface and performance properties.

Because of their unusually high surface activity, coupled with their hydrotropicity and solubilization properties, compounds of this invention will provide exceptionally high performance properties, at very low concentration, in practical applications such as detergency emulsification, solubilization, dispersancy, hydrotropicity, foaming and wetting. In addition, due to their extremely low monomer concentration at use levels, because of their extremely low CMC and $pC_{20}$ values, use of one to two orders of less amounts of the compounds of the invention (compared to conventional surfactants) can provide extremely low or no irritancy in personal care applications.

The unusually high surface activity of the anionic surface active agents of the invention make them the surfactants of choice in enhancing the surface activity of mixtures containing other conventional zwitterionic, amphoteric, nonionic and cationic surfactants. It has been surprisingly found that the compounds of the invention can be mixed with cationic surfactants to form stable blends. This is a significant improvement in the art of forming the surfactant blends which are normal in commercial products.

The properties of enhancement of surface activity, solubilization, and wetting of blends, even when used in small concentrations, can have a wide applicability in industrial, personal care, and pharmaceutical applications where the use of the compounds of the invention, in combination with other conventional surfactants, can provide improved performance blends.

Although the subject invention has been described with respect to a preferred embodiment, it will be readily apparent to those having ordinary skill in the art to which the invention pertains that changes and modifications may be made thereto without departing from the spirit or scope of the subject invention as defined by the appended claims.

What is claimed is:

1. Bis-alkylphenol ethoxylated gemini surfactants characterized as mild and environmentally benign comprising compounds of the formula:

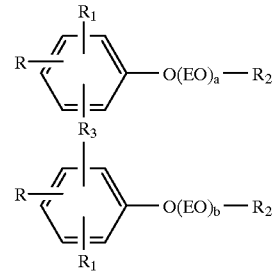

wherein R independently represents alkyl of from 4 to 20 carbon atoms, $R_1$ independently represents hydrogen and alkyl of from 4 to about 20 carbon atoms; $R_2$ independently represents —$SO_3M$, —$P(O)(OM)_2$, —$CH_2COOM$, or $CH_2CHOHCH_2$—$SO_3M$, wherein M represents hydrogen, alkali metal, ammonium or an organic base salt; $R_3$ represents alkylene of from 1 to 10 carbon atoms or —C(O)—$R_4$—C(O)— wherein $R_4$ represents alkylene of from 1 to about 10 carbon atoms or aryl, EO represents ethyleneoxy radicals and wherein "a" and b are numbers of from 0 to about 100, with the proviso that when $R_2$ is sulfonate and $R_3$ is alkylene, $R_1$ represents hydrogen.

2. The surfactants of claim 1, wherein R independently represents straight or branched alkyl of from about 6 to about 10 carbon atoms.

3. The surfactants of claim 1, wherein $R_1$ is hydrogen.

4. The surfactants of claim 1, wherein $R_2$ is —$SO_3M$, or —$P(O)(OM)_2$.

5. Surfactants of claim 1, wherein $R_3$ represents lower alkylene of from 1 to 4 carbon atoms.

6. The surfactants of claim 1, wherein $R_3$ represents —C(O)—$R_4$—C(O)—.

7. The surfactants of claim 1, wherein $R_4$ is alkylene.

8. The surfactants of claim 1, wherein $R_4$ is phenylene.

9. The surfactants of claim 1, wherein $R_2$ is —$SO_3M$ or —$P(O)(OM)_2$.

10. The surfactants of claim 1, wherein said organic base salt is derived from a base selected from the group consisting of monoethanolamine, diethanolamine, triethanolamine, triethylamine, trimethylamine and N-hydroxyethyl morpholine.

11. The surfactants of claim 1, wherein M in Formula I is the alkali metal sodium.

12. The surfactants of claim 1, wherein said surfactant comprises compounds of the formula:

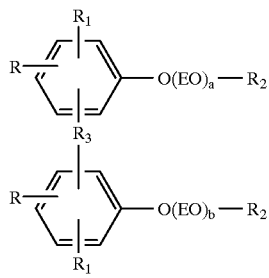

II wherein $R_3$ is alkylene of from 1 to 10 carbons.

13. The surfactants of claim 1, wherein said surfactant comprises compounds of the formula:

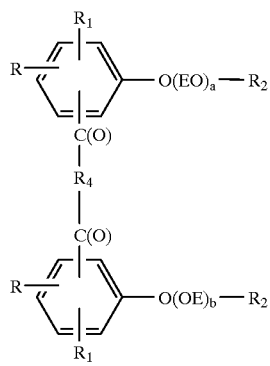

III

14. A cleaning composition comprising an aqueous solution having a cleaningly effective amount of the composition of claim 1 dissolved therein.

15. The cleaning composition of claim 14, wherein the solution is selected from the group consisting of hair shampoos, baby shampoos, body shampoos, bubble baths, bar soaps, bath gels, hair conditioning gels, skin creams and lotions, skin contacting cosmetics, make up removal creams and lotions, liquid detergents, dish detergents, liquid soaps, bleach activators and bleach stabilizers.

16. The surfactants of claim 1 wherein "a" is from 1 to 30.

17. The surfactants of claim 1 wherein "a" is from 1 to 30.

18. The surfactants of claim 1 wherein "a" is 5.

19. The surfactants of claim 1 wherein "a" is 9.

20. The surfactants of claim 1 wherein "a" is 10.

21. The surfactants of claim 1 wherein "a" is 11.

22. Bis-alkylphenol ethoxylated gemini surfactant characterized as mild and environmentally benign comprising a compound of the formula:

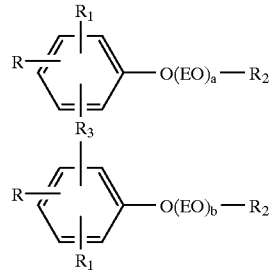

wherein R independently represents alkyl of about 6 to 10 carbon atoms, $R_1$ is hydrogen; $R_2$ is —$SO_3M$, or —$P(O)(OM)_2$, wherein M represents hydrogen, alkali or alkaline earth metal, ammonium or an organic base salt; $R_3$ represents methylene, and wherein "a" is number of from 0 to about 30.

23. The surfactants of claim 22 wherein $R_2$ is —$SO_3M$.

24. The surfactants of claim 23 wherein R "a" is 10.

25. The surfactants of claim 22 wherein $R_2$ is —$P(O)(OM)_2$.

26. The surfactants of claim 23 wherein "a" is 10.

* * * * *

UNITED STATES PATENT AND TRADEMARK OFFICE
CERTIFICATE OF CORRECTION

PATENT NO. : 5,922,671
DATED : July 13, 1999
INVENTOR(S) : David James Tracy; Ruoxin Li; Jean-Marc Ricca It is certified that error appears in the above-identified patent and that said Letters Patent is hereby corrected as shown below:

On the title page item [57],
In the Abstract, at the first line following the formula, after "R independently represents", delete "alkali" and insert therefore -- alkyl --.

In the Abstract, at the second line following the formula, after "represents hydrogen", delete "EO represents ethyleneoxy radicals" and insert therefor -- and --.

In the Abstract, at the fifth line following the formula, after "M represents hydrogen," delete "alkyl", and insert therefor -- alkali --.

In the Abstract, at the eleventh line following the formula, after "R is not hydrogen," insert -- EO represents ethyleneoxy radicals, --.

Signed and Sealed this

Twenty-ninth Day of February, 2000

Attest:

Q. TODD DICKINSON

*Attesting Officer*  *Commissioner of Patents and Trademarks*